United States Patent
Abed Aljawad et al.

(10) Patent No.: US 10,248,197 B2
(45) Date of Patent: Apr. 2, 2019

(54) SYSTEMS AND METHODOLOGIES FOR REAL TIME EYE TRACKING FOR ELECTRONIC DEVICE INTERACTION

(71) Applicant: Imam Abdulrahman Bin Faisal University, Dammam (SA)

(72) Inventors: Dania Ali Abed Aljawad, Dammam (SA); Ebtesam Jubran Alqahtani, Dammam (SA); Ghaidaa Mohammad Al-Kuhaili, Dammam (SA); Nada Mohammed Qamhan, Dammam (SA); Noof Abdullah Alghamdi, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 15/499,296

(22) Filed: Apr. 27, 2017

(65) Prior Publication Data

US 2018/0314324 A1    Nov. 1, 2018

(51) Int. Cl.
*G06F 3/01* (2006.01)
*A61B 3/113* (2006.01)
(Continued)

(52) U.S. Cl.
CPC .............. *G06F 3/013* (2013.01); *A61B 3/113* (2013.01); *G06T 7/73* (2017.01); *G06F 3/04886* (2013.01);
(Continued)

(58) Field of Classification Search
CPC .... G06F 3/013; G06F 3/0416; G06F 3/04886; G06F 2203/04806; G06T 7/73; G06T 7/80; G06T 2207/30201; A61B 3/113
See application file for complete search history.

(56) References Cited

U.S. PATENT DOCUMENTS

| 9,075,453 B2 | 7/2015 | Bhaskar et al. |
| 2013/0169533 A1* | 7/2013 | Jahnke .................... G06F 3/017 345/158 |

(Continued)

FOREIGN PATENT DOCUMENTS

| EP | 1315113 A1 | 5/2003 |
| EP | 2242419 B1 | 1/2016 |

OTHER PUBLICATIONS

Valenti, R., et al., "Combining Head Pose and Eye Location Information for Gaze Estimation", IEEE Transactions on Image Processing, vol. 21, No. 2, pp. 802-815, (Feb. 2012).

(Continued)

*Primary Examiner* — Amit Chatly
(74) *Attorney, Agent, or Firm* — Oblon, McClelland, Maier & Neustadt, L.L.P.

(57) ABSTRACT

Methods and systems are provided for controlling an electronic device. The method includes acquiring, by a processor of the electronic device, a facial image. The facial image includes a face of a user having one or more eyes. The processor detects a center position of the eye and a pupil position corresponding to a center of a pupil of the eye, determines an eye gaze position based on the center position and the pupil position, analyzes the eye gaze position in consecutively captured facial images, and performs a function associated with a touch event at the eye gaze position in response to determining that the gaze position corresponds to a location of the touch event in the consecutively captured facial images.

20 Claims, 6 Drawing Sheets

(51) Int. Cl.
  *G06T 7/73*      (2017.01)
  *G06T 7/80*      (2017.01)
  *G06F 3/0488*    (2013.01)
(52) U.S. Cl.
  CPC ...... *G06F 2203/04806* (2013.01); *G06T 7/80* (2017.01); *G06T 2207/30201* (2013.01)

(56) References Cited

U.S. PATENT DOCUMENTS

| | | | | |
|---|---|---|---|---|
| 2014/0085204 | A1* | 3/2014 | Jahnke | G06F 3/013 345/158 |
| 2014/0247232 | A1* | 9/2014 | George-Svahn | G06F 3/02 345/173 |
| 2015/0293588 | A1* | 10/2015 | Strupczewski | G06T 17/10 382/117 |
| 2016/0117544 | A1* | 4/2016 | Hoyos | H04N 5/23219 348/78 |
| 2016/0202756 | A1* | 7/2016 | Wu | G06F 3/013 382/103 |
| 2016/0210503 | A1 | 7/2016 | Yin et al. | |

OTHER PUBLICATIONS

Ince, I.F., et al., "A 2D Eye Gaze Estimation System with Low-Resolution Webcam Images", EURASIP Journal on Advances in Signal Processing, vol. 40, 20 Pages total, (Aug. 12, 2011).

* cited by examiner

SYSTEMS AND METHODOLOGIES FOR REAL TIME EYE TRACKING FOR ELECTRONIC DEVICE INTERACTION

BACKGROUND

Smart devices are being extensively used due to their many benefits. Many smart devices available in the market have input methods involving physical contact (e.g., touch, swipe). Some people may want to use non-contact input methods for various reasons (e.g., because of an injury or disability). Unfortunately, many smart devices lack the capability to support disabled users who cannot touch the screen of a smart device, depriving the disabled users from the benefits of smart devices.

The foregoing "Background" description is for the purpose of generally presenting the context of the disclosure. Work of the inventor, to the extent it is described in this background section, as well as aspects of the description which may not otherwise qualify as prior art at the time of filing, are neither expressly or impliedly admitted as prior art against the present invention.

SUMMARY

According to an embodiment of the present disclosure, there is provided a method for controlling an electronic device. The method includes acquiring, by a processor of the electronic device, a facial image. The facial image includes a face of a user having one or more eyes. Further, the method includes detecting, in response to detecting an eye within the facial image, a center position of the eye, detecting, in response to detecting an eye within the facial image, a pupil position corresponding to a center of a pupil of the eye, determining, by the processor and based on the center position and the pupil position, an eye gaze position, and analyzing the eye gaze position in consecutively captured facial images. The method further includes performing a function associated with a touch event at the eye gaze position in response to determining that the eye gaze position corresponds to a location of the touch event in the consecutively captured facial images.

According to an embodiment of the present disclosure, there is provided a system including a camera and a processor. The processor is configured to detect a center position of an eye within a facial image captured via the camera in response to detecting an eye within the facial image. The facial image includes a face of a user having one or more eyes. The processor is further configured to detect the pupil position of the eye in the facial image in response to detecting an eye within the facial image, deter mine an eye gaze position based on the center position and the pupil position, analyze the eye gaze position in consecutively captured facial images, and perform a function associated with the touch event at the eye gaze position in response to determining that the gaze position corresponds to a location of the touch event in the consecutively captured facial images.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Referring now to the drawings, wherein like reference numerals designate identical or corresponding parts throughout several views, the following description relates to a system and associated methodology for controlling a device based on real time eye tracking.

The system described herein may run in the background of an electronic device's system and continuously receive captured frames from a camera of the electronic device. The methodology described herein determines an eye gaze position based on an association between a user's eye center and a center of the device's display. The system may estimate a position of a user's gaze based on a gaze position of a left eye. In other implementations, the system may rely on the right eye or a combination of data associated with both the right eye and the left eye. The method considers that the center of the eye corresponds to the center of the screen (i.e., display of the electronic device) and then calculates a displacement between the center of the eye and a pupil of the eye with respect to x and y axes. The calculated displacement is then scaled based on the display's size. If a user gazes a specific point on the screen for a certain period of time, the system automatically performs a function associated with a touch event at the gazing position. The touch event corresponds to an area of the electronic device that would have been touched by a user to activate a function of the electronic device. The system outputs a visual indicator on the display that moves as a function of the movement of the user's eyes, which helps the user tracks the movement of the eyes with respect to the display.

Figure 1:
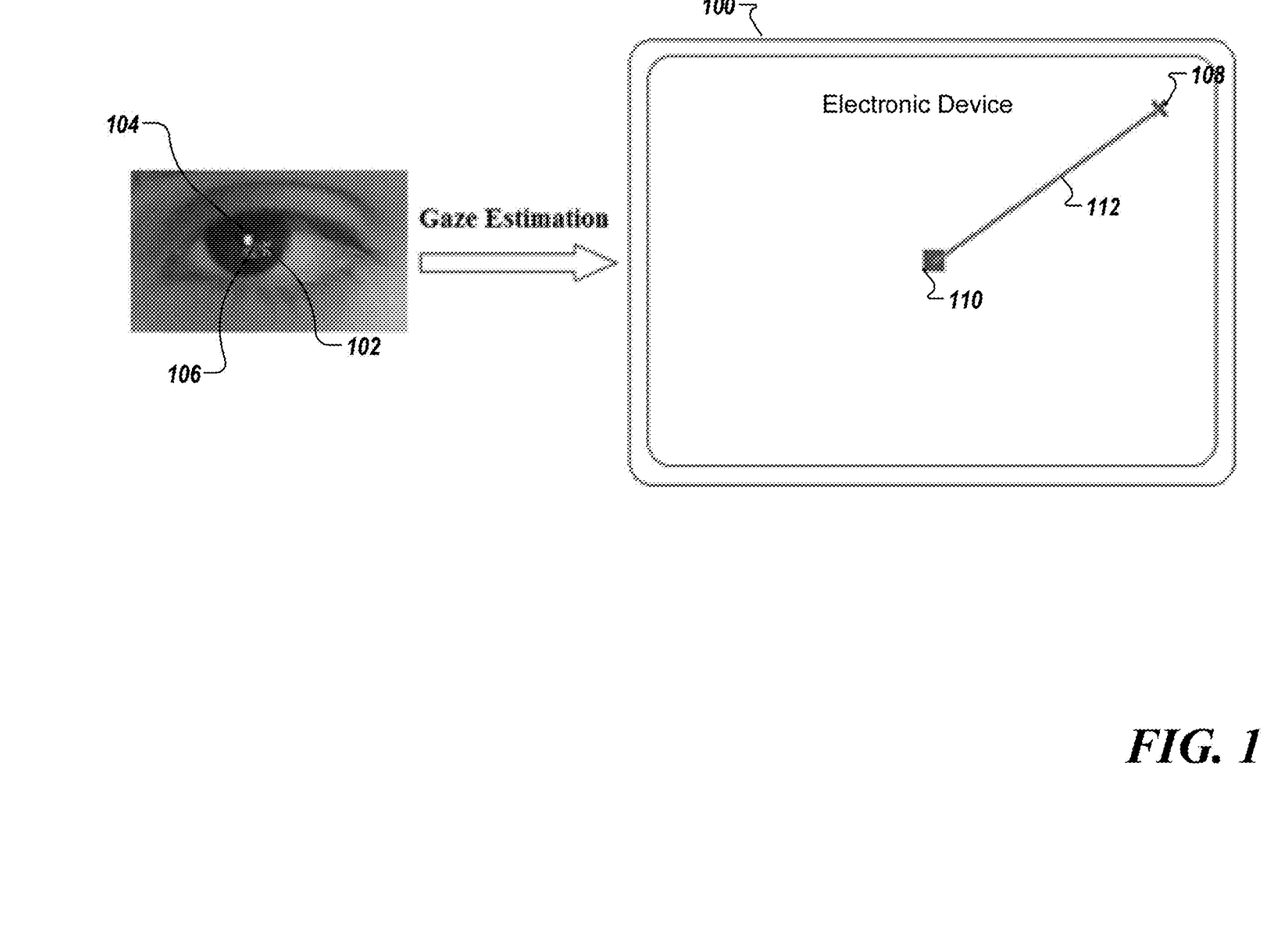
FIG. 1 is a schematic that shows an electronic device controlled by real time eye tracking according to one example.
Figure 6:
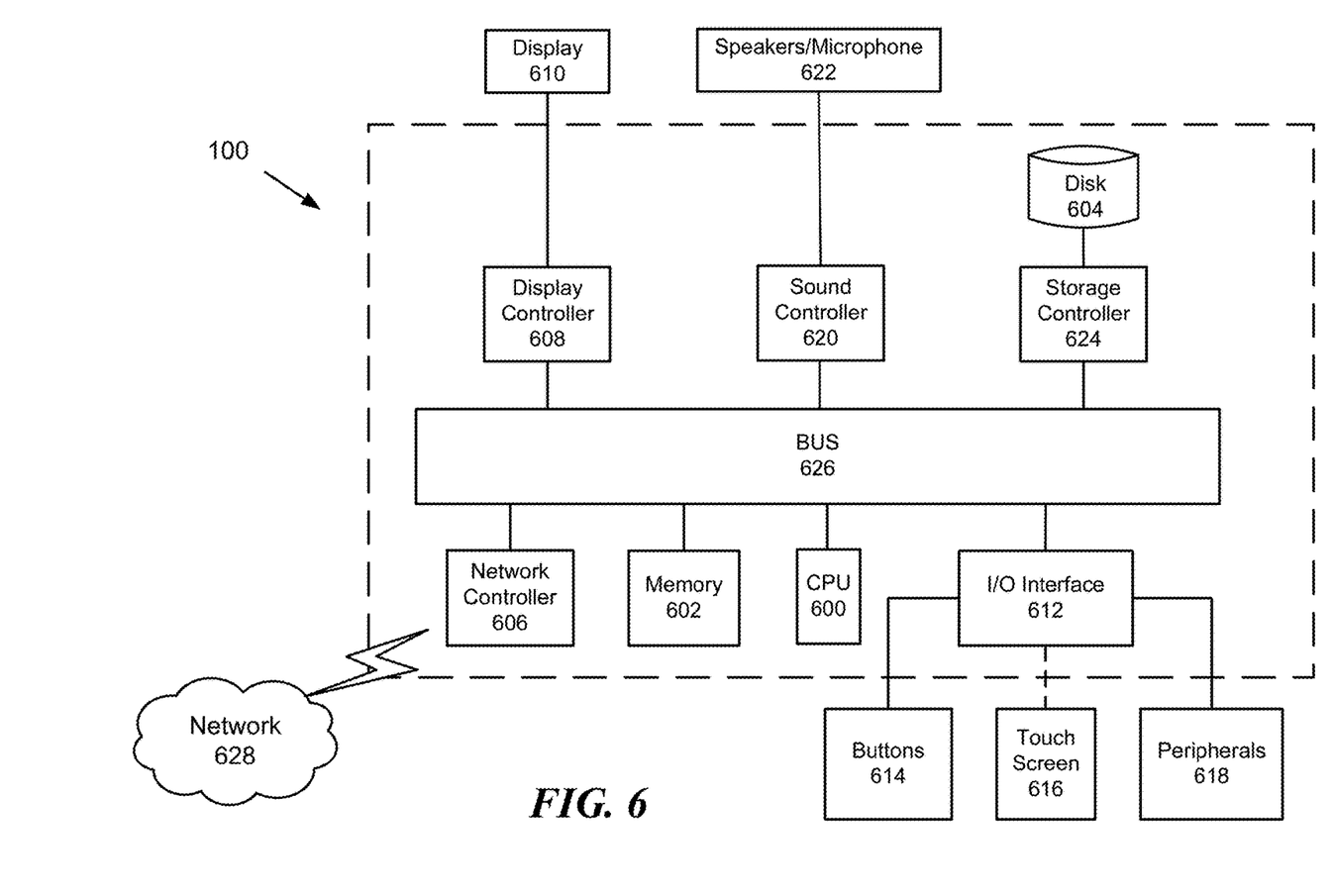
FIG. 6 is an exemplary block diagram of the electronic device according to one example.

FIG. 1 is a schematic that shows an electronic device 100 controlled by real time eye tracking according to one example. The electronic device 100 may include a desktop computer, a laptop computer, a tablet computer, a smart phone, or other similar device. The real time eye tracking methodologies described herein may also be incorporated into a gaming device, into a television display, into vehicles to control dashboard, or the like. The electronic device 100 includes a CPU 600 connected to or otherwise in communication with a display device 610 and a memory 602 as shown in FIG. 6. The electronic device 100 further includes or is connected to a camera. In one example, the camera of the electronic device 100 has a resolution of at least two megapixels but can also be configured to obtain images having resolutions greater than or less than two megapixels.

The center of the left eye is indicated by 102 in FIG. 1. The center of the pupil is indicated by 104. The displacement between the center 102 of the eye and the pupil 104 of the eye is indicated by 106. FIG. 1 shows the mapping of a user gaze to a visual indicator 108 on the display of the electronic device 100. The center of the display of the electronic device 100 is indicated by 110. The displacement 112 from the center 110 of the display is a function of the displacement 106 between the pupil and the center of the eye.

Figure 2:
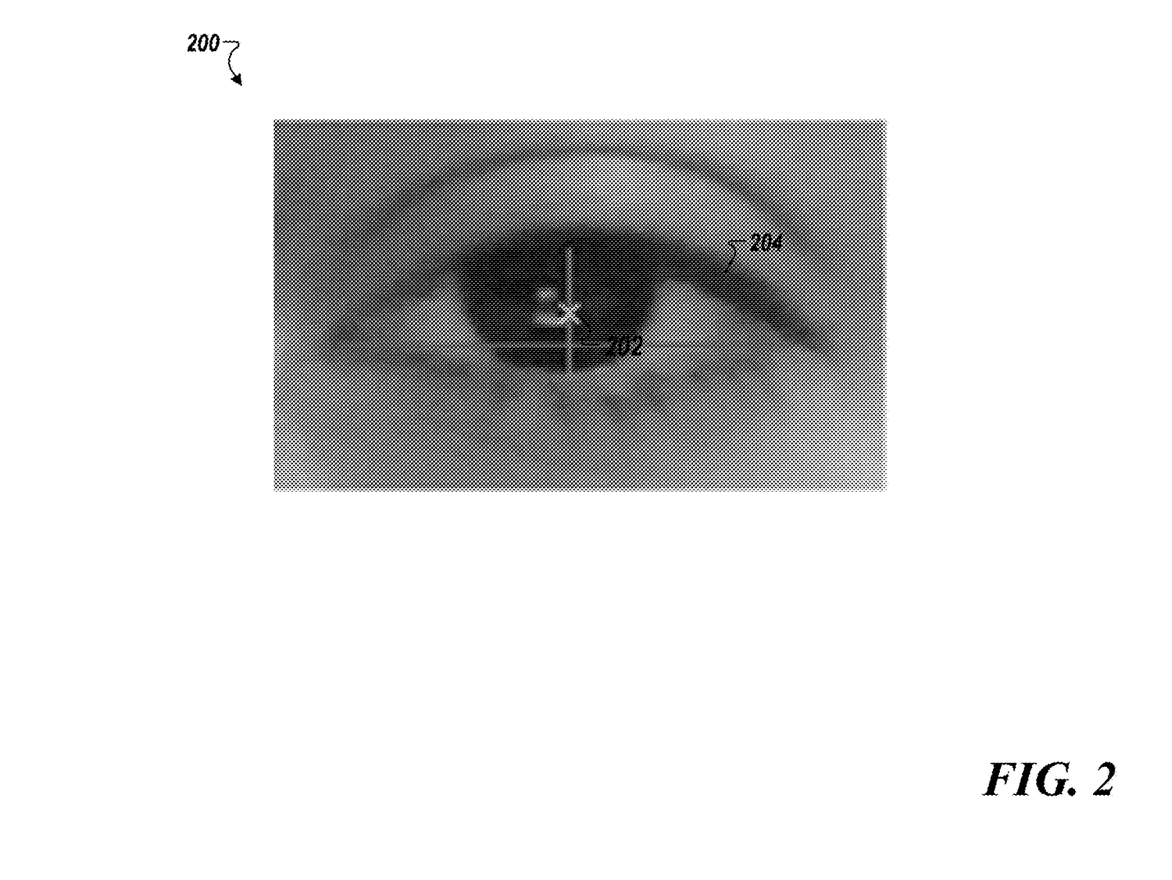
FIG. 2 is a schematic that shows the center of an eye according to one example.

FIG. 2 is a schematic 200 that shows the center 202 of an eye 204 according to one example. A location of the center 202 of the eye is different from a pupil location unless the user gazes in such a way that makes the center of the eye and the pupil appear at the same exact position in the received facial image. The center 202 is at the middle of the eye, i.e., the center of the eye is at the middle of the horizontal vector connecting the eye's corners and at the middle of the vertical vector connecting the eyelids. For example, the x-coordinate of the eye's center is the x-coordinate of the center of the horizontal line, and the y-coordinate of the eye's center is the y-coordinate of the center of the vertical line. The center 202 of the eye may be calculated based on actual eyeball diameter and an actual face size of the user determined from detected facial features using image processing techniques (e.g., template-matching methods, Eigen faces, Hidden Markov Model) or by using statistics stored in the memory of the electronic device 100.

Figure 3:
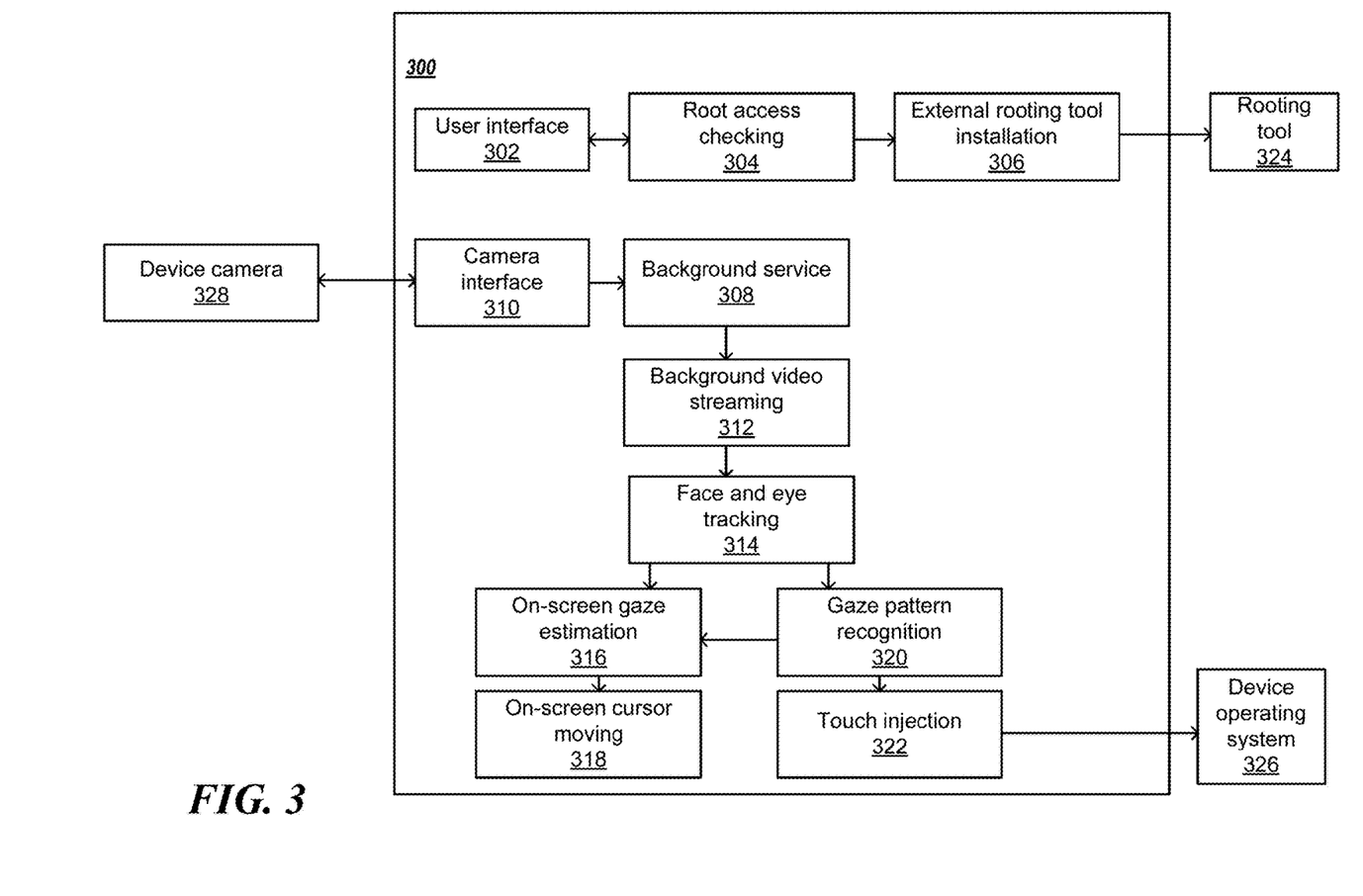
FIG. 3 is a block diagram of a system for controlling the electronic device based on real time eye tracking according to one example.

FIG. 3 is a block diagram of a system 300 for controlling the electronic device 100 based on real time eye tracking according to one example. The system 300 includes a user interface module 302, a root access checking module 304, an external rooting tool installation module 306, a background service module 308, a camera interface module 310, a background video streaming module 312, a face and eye tracking module 314, an on-screen gaze estimation module 316, an on-screen cursor moving module 318, a gaze pattern recognition module 320, and a touch injection module 322.

Each of the modules described herein may be implemented in circuitry that is programmable (e.g. microprocessor-based circuits) or dedicated circuits such as application specific integrated circuits (ASICS) or field programmable gate arrays (FPGAS). In some implementations, the processes associated with each of the modules may be performed by one or more processors of a server or other computing resources, which can include cloud computing resources. The user interface module 302 represents the user interface that makes using the system 300 user-friendly. The interface may include two buttons, a "Start" button and a "Stop" button. The "Start" button initiates an eye gazing mode in the background and exits the application's interface in order to allow the user to start controlling other applications using his/her eyes. Throughout the disclosure, references to processes performed in the background refer to processes that are executed without a corresponding user interface being displayed on a screen of the device. The "Start" button may be activated by a finger touch since the eye gazing mode is not yet activated by the system 300. Once the system 300 is activated the user can control the electronic device 100 using gazing patterns of his/her eyes. If the user wants to stop the system, the user selects or opens the user interface of the system 300, for example, by gazing at or touching an icon associated with the system, then gazing at or touching the "Stop" button. After stopping the system 300, the eye gazing mode is terminated and the user may not be able to control the electronic device 100 through eyes gestures unless the system 300 is activated.

Current conventions of some operating systems (e.g., Android operating systems) prohibit touch injection by user applications like the system described herein unless the device is rooted. Then, the system can initiate a super user mode through the Linux command "su". Only system applications which are signed with the key of the device's manufacturer can do that without having the device rooted. Obtaining the key of a manufacturer may be hard and make the system device-dependent (i.e., system works on specific devices which belong to a certain manufacturer). Thus, the system 300 may run on a rooted device. The root access checking module 304 may check whether the electronic device 100 is rooted or not.

The root access checking module 304 is activated in response to activation of the system 300 (e.g., by touching an application icon associated with the system). In response to determining that the electronic device 100 is rooted, the interface described previously herein is outputted on the display. Otherwise, the system 300 may prompt a message to the user indicating that the electronic device 100 has to be rooted to run the system properly. In response to the system 300 receiving an indication that the user accepts the prompt message (e.g., by touching an "OK" button), the root access checking module 304 may initiate the external rooting tool installation module 306 to install a third party rooting application that allows the user to root the electronic device 100 through a user-friendly graphical user interface instead of impelling the user to go through complicated code-based rooting procedures. After the rooting process is completed, the system 300 may be activated (e.g., by opening an application associated with the system). Then, the eye gazing mode is activated.

In response to activation of the "Start" button, the background service module 308 is initiated which is responsible for running all image processing and eye gazing mode tasks. A service class in Android application development may run in the background while the user performs other tasks, for example, using other applications. This technique allows tracking the user's eyes and simulating a touch event once a gazing pattern is recognized. For example, while the camera 328 and the eye gazing mode are running in the background, the user can gaze at the icon of an application, and that gazing pattern may be tracked and recognized by several modules of the system 300. Then, a touch event can be simulated at the gazing point on the display.

Once the background module 308 is activated, the camera interface module 310 starts operating. The camera interface module 310 performs camera related operations such as checking for an existence and/or operational capability of the camera 328, activating the camera 328, deactivating the camera 328, and receiving video frames from the camera 328 of the electronic device 100. The camera interface module 310 operates in the background, in which the camera 328 continuously captures frames without user interference. When the eye gazing mode is activated, the camera interface module 310 continuously receives the captured frames from the camera 328 at a predetermined capture rate. The received frames are sent to the background video streaming module 312 to be processed.

A function of the background video streaming module 312 is to receive the frames captured via the camera 328 of the electronic device 100. Every frame may be received by default as a byte array. Every frame is converted initially to a bitmap due to an ease of conversion from bitmap to other data structures used by the associated algorithms and libraries to process the frame content. After the frame is converted to a bitmap, the frame may be sent to the face and eye tracking module 314.

In some implementations, the face and eye tracking module 314 can perform two tasks. A first task includes determining the center of the eye in each received frame when a face is detected in the frame. The center of the eye determined by the face and eye tracking module 314 is used to identify the displacement of the pupil from the center of the eye in terms of x and y coordinates and hence the corresponding displacement from the center of the screen. The system 300 may analyze only one face in every frame. When more than one face is detected, no face is detected, or the eye is not opened, the system 300 may not perform further image processing tasks and may output a corresponding message to help the user take a corrective action. Once a face is detected, a location of the eye (e.g., predefined eye left or right eye) is determined within the detected face, then the center of the eye is found in terms of x and y coordinates in the received frame.

A second task is to detect the eye pupil to be able to calculate its displacement from the center of the eye as stated previously. First, the face is detected, then the eyes' region is detected, after that the iris of every eye is detected, and finally the pupil is found as the darkest object in every eye, because the pupil is substantially black in color. For example, the captured frame may be transformed to a grayscale image. The intensity of each pixel is expressed within a given range between a minimum and a maximum. The minimum intensity may be associated with "black" and the maximum associated with "white". The pixel with the lowest intensity value corresponds to the location of the center of the pupil. The center of the pupil position is defined as x any y coordinates in the received frame. In one example, the face is detected using a Haar Cascade Classifier which uses feature selection techniques to detect different objects in images. The x and y coordinates of the eye's center and pupil are used for estimating the gaze position on the screen as described later herein.

The on-screen gaze estimation module 316 determines the gazing position on the display based on the displacement of the pupil from the center of the eye in terms of x and y offsets. The on-screen gaze estimation module 316 maps the displacement of the pupil from the center of the eye to a displacement from the center of the screen in terms of x and y offsets. The center of the eye represents the center of the screen, and is a reference point based on which the displacement from the center of the screen is determined. The displacement between the eye's center and pupil with respect to the x axis is the difference between the x coordinates of the pupil and the center of the eye, while the displacement with respect to the y axis is the difference between the y coordinates of the pupil and the center of the eye. Since the positions of the eye's center and pupil are found within the received frame which can contain other objects captured by the camera, the displacement may be determined after processing the frame considering that the eye region occupies a small region of the entire frame. For example, the processing can include scaling up positions of the eye's center and pupil with respect to an eye region found in the frame. To scale up the positions, a scaling factor for the x coordinates is determined which may be, in one example, a ratio of the frame's width to the eye region's width. Similarly, the scaling factor for the y coordinates may be the ratio of the frame's height to the eye region's height. The scaling factors for x and y coordinates may be expressed as:

$$\text{Scaling factor}_X = \text{Width}_{Frame}/\text{Width}_{eye's\ region} \quad (1)$$

$$\text{Scaling factor}_Y = \text{Height}_{Frame}/\text{Height}_{eye's\ region} \quad (2)$$

After determining the scaling factors, the scaled x and y positions for the pupil and the center of the eye are determined. The scaled x coordinate of the pupil is its unscaled x coordinate multiplied by the calculated scaling factor for the x axis, while the scaled y coordinate of the pupil corresponds to the unscaled y coordinate multiplied by the calculated scaling factor for the y axis. Similarly, the x and y coordinates of the eye's center are scaled. Equations 3 and 4 show the calculation of the scaled positions of the eye's pupil and center respectively.

$$\text{Pupil}(X_{Scaled}, Y_{Scaled}) = \text{Pupil}(X_{old} \times \text{Scaling factor}_X, Y_{old} \times \text{Scaling factor}_Y) \quad (3)$$

$$\text{Center}(X_{Scaled}, Y_{Scaled}) = \text{Center}(X_{old} \times \text{Scaling factor}_X, Y_{old} \times \text{Scaling factor}_Y) \quad (4)$$

After determining the scaled positions of the eye's pupil and center, the displacement with respect to the x axis is calculated as the difference between the x coordinates of the pupil and the center. Similarly, the displacement with respect to the y axis is the difference between the y coordinates of the pupil and the center. The resulted displacements may be multiplied by a predetermined scaling factor n. The predetermined number n is determined during testing of the system, where if multiplying the displacement with the scaling factor n is found to be useful in enhancing the results, the value of n is determined (optimized) as the one that yields the best results. Calculating the displacement with respect to the x axis and with respect to the y axis is shown in equations 5 and 6 respectively. Parts enclosed with braces '{ }' are optional.

$$\text{Displacement}_X = [-[\text{Pupil}(X_{Scaled}) - \text{Center}(X_{Scaled})]]\{\times n\} \quad (5)$$

$$\text{Displacement}_Y = [\text{Pupil}(Y_{Scaled}) - \text{Center}(Y_{Scaled})]\{\times n\} \quad (6)$$

In equation (5), the displacement with respect to x axis is multiplied by −1, because the captured frame may be horizontally flipped. For example, if a user is actually looking to the right, the pupil appears oriented to the left in the received frame. Due to the horizontal flipping of the captured frame, the calculated displacement with respect to the x axis must be multiplied by −1. Based on equation (5), displacement x can be zero, negative, or positive. The displacement x is negative if the user gazes to the left of the screen, positive if the user gazes to the right of the screen, and zero if he/she gazes exactly at the horizontal center of the screen. Similarly, displacement y can be zero, negative, or positive. The displacement y is positive if the user gazes at the top of the screen, negative if he/she gazes at the bottom of the screen, and zero if he/she gazes at the vertical center of the screen.

The calculated x and y displacements are calculated with respect to the eye region and optionally scaled by a predetermined scaling factor n. To calculate the x and y displacements on the screen, the calculated x and y displacements are scaled to fit in a range of the predetermined horizontal and vertical displacement on the device's screen.

Calculating the ranges of the horizontal and vertical displacements on the screen is a function of the screen's width, height d center coordinates. Since the horizontal displacement is determined from the screen's center, the maximum horizontal displacement on the screen is half of the screen width to the right or to the left of the center, while the minimum x displacement is zero if the user looks at the horizontal center of the screen. Similarly, the maximum y displacement on the screen is half of the screen height above or below the screen's center, while the minimum y displacement is zero, if the user looks at the vertical center of the screen.

The display's width and height may be obtained when the system 300 is activated. The center coordinates are calculated based on the display's dimensions. The x coordinate of the center is calculated as half of the width of the screen, while the y coordinate is calculated as half of the height of the screen. The equation below illustrates the calculated center coordinates:

$$\text{Center}_{Screen}=(\text{Width}_{Screen}/2, \text{Height}_{Screen}/2) \quad (7)$$

In one implementation, the center's coordinates are stored in the memory 602.

The scaling function that is used to scale up the x and y displacements values may be expressed as:

$$\text{Value}_{Scaled}=\text{Max}_{Scaled} \times \log_{10}(\text{Value}_{Unscaled}+1)/\log_{10}(\text{Max}_{Unscaled}+1) \quad (8)$$

where $\text{Value}_{Scaled}$ is the new scaled up displacement value, $\text{Max}_{Scaled}$ is the upper bound of the scaled range of displacement values, $\text{Value}_{Unscaled}$ is the displacement value obtained from the eye region, and $\text{Max}_{Unscaled}$ is the upper bound of the unscaled range of displacement values. The lower bound of the unscaled and scaled ranges of displacement values is 0, and if the unscaled value of the displacement is 0, the scaled calculated displacement according to the used function is also 0, because $\log_{10}(1)=0$. This function is applied twice, one time to scale up the x displacement, and the second time to scale up the y displacement. Other scaling functions that can produce good results may be used instead of the one illustrated by equation (8).

The maximum scaled values for the x and y displacements are half of the screen's width and half of the screen's height respectively as stated previously. Calculating the unscaled value of x and y displacements depends on a fact that the obtained position of the eye's center is located at the center of the horizontal vector that connects the two corners of the eye and at the center of the vertical vector that connects the upper and lower eyelids. Based on this fact, the maximum horizontal displacement from the center of the eye is half of the horizontal vector which connects the two corners of the eye magnitude to the left or right of the center, while the maximum vertical displacement is half of the vertical vector which connects the upper and lower eyelids magnitude above or below the center.

After calculating the scaled x and y displacements, the gaze position on the screen s calculated by adding the scaled x displacement to the x coordinate of the center of the screen and the scaled y displacement to the y coordinate of the center of the screen. As a result of this addition, the gaze position moves left if the x displacement is negative, while it moves right if it is positive. On the other hand, the gaze position moves down if the y displacement is negative, whereas it moves up if the y displacement is positive. Every time the on-screen gaze estimation module 316 determines the on-screen gaze position, the on-screen gaze estimation module 316 sends it to the on-screen cursor moving module 318 to move a visual indicator (e.g., cursor) to the recently calculated gaze position.

The on-screen cursor moving module 318 continuously receives the calculated on-screen gaze position from the on-screen gaze estimation module 316 and updates the position of visual indicator on the screen accordingly.

The gaze pattern recognition module 320 receives the coordinates of the eye's (e.g., left eye's) pupil in every frame calculated by the face and eye tracking module 314. Detecting the pupil at the same position in a predetermined number of consecutive frames (e.g., four consecutive frames) indicates that the user is gazing at a specific position on the screen and indicates that a gaze pattern is recognized. The pupil's position identified in the first received frame is compared to the pupil's position identified in each of the predetermined number of consecutive frames. If the comparison of any of the consecutive frames with the first frame matches, then the pupil's position identified in that frame is stored. In one example, when a gaze pattern is identified, an average of the stored pupil positions is determined. Calculating the average in this case provides an accurate generalized pupil's position, where taking into consideration small differences that may occur between the pupil's positions in the consecutive frames. If any of the comparisons does not match, then no gaze pattern is identified.

In some instances, the user's pupil does not stay at exactly the same x and y coordinates even if the user is gazing at a specific point on the screen, which can result in slight differences in the pupil's positions in consecutive frames. Thus, a tolerance of the pupil's position is defined, i.e., if the comparison between two pupil positions yields a difference equal to the tolerance value or less, then the comparison is passed, otherwise the comparison fails.

Figure 4:
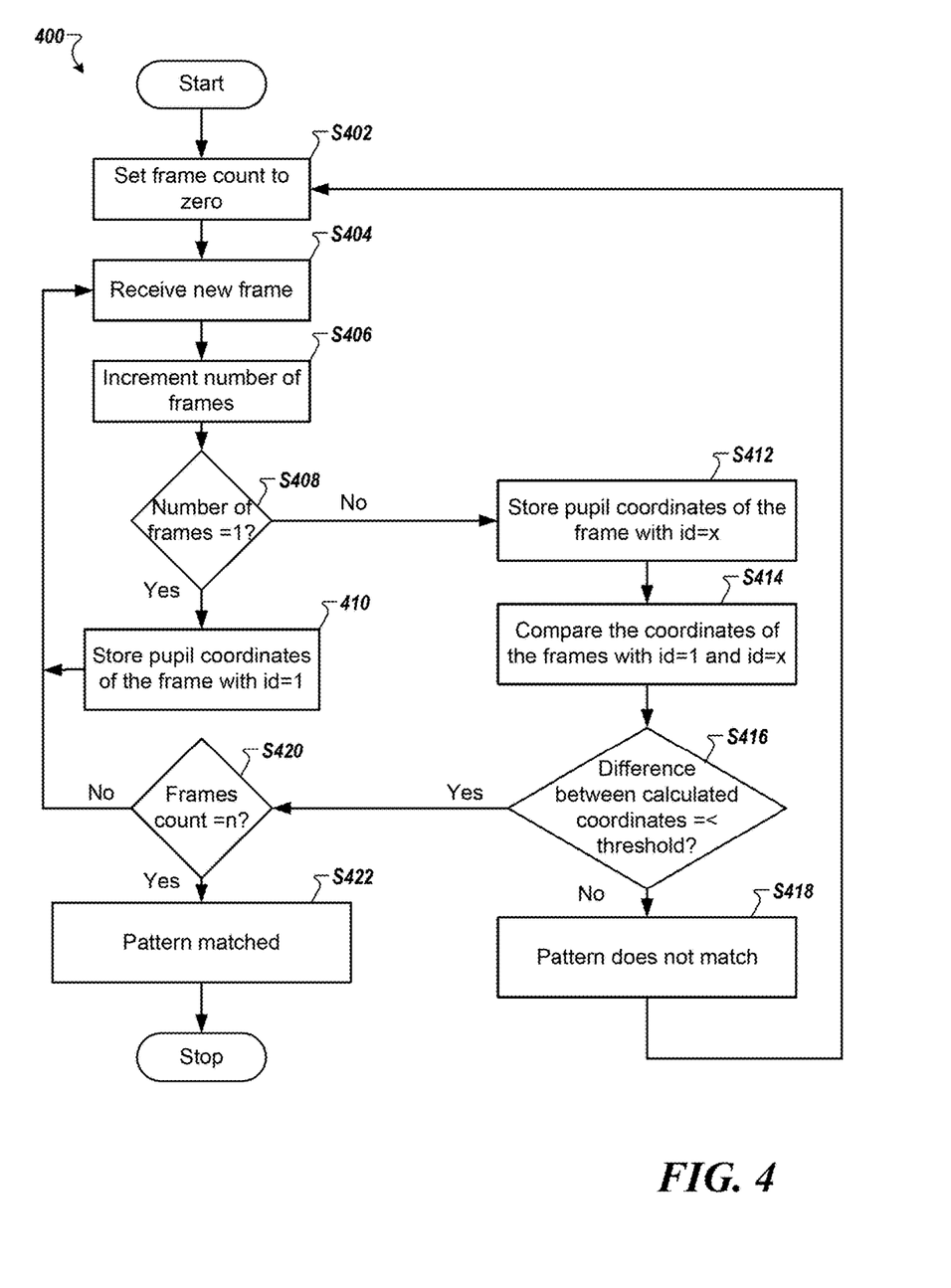
FIG. 4 is a flowchart of a method for gaze pattern recognition according to one example.

If a gaze pattern is identified (e.g., a comparison match is detected), the CPU 600 calculates the average of the pupil's position in the consecutive frames and sends it to on-screen gaze estimation module 316 to calculate the gaze position based on the determined averaged pupil's position and the center of the eye in the current frame. The determined gaze position is sent to on-screen cursor moving module 318 to move the visual indicator to the obtained gaze position, then to the touch injection module 322 to inject a touch event at the calculated gaze position. FIG. 4 depicts the method executed by the gaze pattern recognition module 320.

The touch injection module 322 injects a touch event into the device's system at the calculated gaze coordinates which causes a touch event to take place at that position without the need of physically touching the screen.

Figure 5:
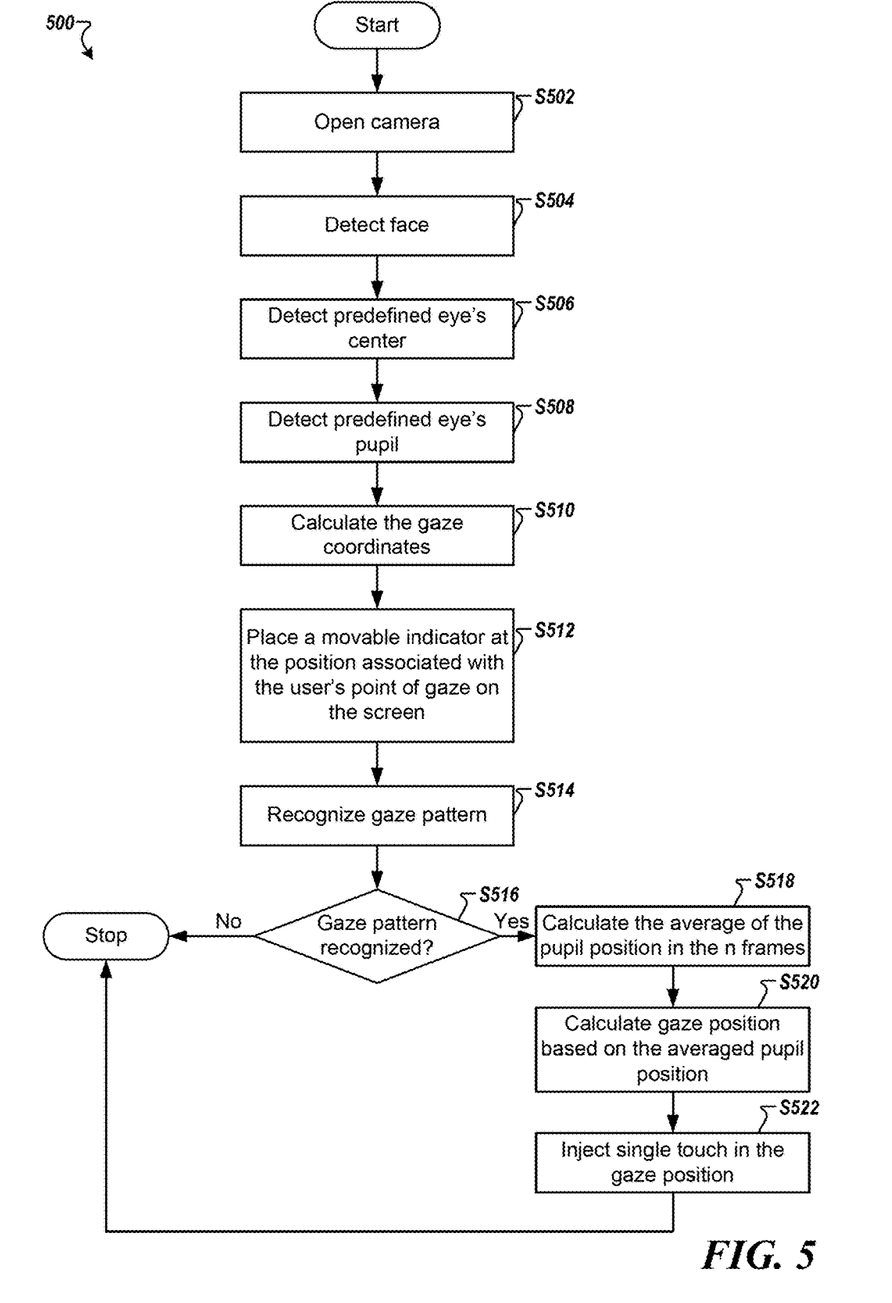
FIG. 5 is a flowchart of a method for controlling the electronic device based on real time eye tracking according to one example.

Soft keys for home button, back button, left swipe, right swipe, upwards swipe, downwards swipe, and a soft key for opening the notification bar content may be provided on the display. The user can gaze at any of the soft keys and the system performs a single touch at the position of the soft key, which results in performing the action associated with the key. For example, if the user gazes at the home soft key, the application injects a touch event that results in returning back to the home screen. FIG. 5 shows the flow chart of the method for controlling an electronic device.

In one example, when the gaze location is associated with performing tasks that consist of two or more functions such as a double tap, 3D touch, or the like, additional soft keys associated with these tasks may be overlaid on the display. Alternatively, additional gaze patterns that correspond to performing such tasks can be used.

FIG. 4 is a flow chart that shows a method 400 for gaze pattern recognition according to one example. At step S402, a frame count is initialized. For example, the frame count may be set to zero. At step S404, a frame is received. The frame may be a part of a sequence of frames captured by the camera.

At step S406, the frame count is incremented by a predefined incremental value (e.g., one). At step S408, the processor may check whether the frame count is equal to a predetermined number (e.g., one). In response to determining that the frame count is equal to the predetermined number, the process proceeds to step S410. In response to determining that the frame count is not equal to the predetermined number, the process proceeds to step S412.

At step S410, the center of pupil coordinates associated with the frame are stored in association with the frame identification number (e.g., frame 1). Then, the process proceeds to step S404.

At step S412, the center of pupil coordinates associated with the frame received at step S404 are stored. The center of pupil coordinates may be determined as described previously herein.

At step S414, the center of the pupil coordinates of the initial frame and the frame received at step S404 are compared. At step S416, a determination is made whether the difference between the center of the pupil coordinates of the initial frame and the center of the pupil coordinate of the frame received at step S404 is below a predetermined threshold. In response to determining that the difference is above the predetermined threshold, the process proceeds to step S418. In response to determining that the difference is below the threshold, the process proceeds to step S420.

At step S418, a determination is made that the pattern does not match and the process proceeds to step S402.

At step S420, the processor checks whether the frame count is equal to another predetermined number. In response to determining that the frame count is equal to the another predetermined number, the process proceeds to step S422. In response to determining that the frame count is not equal to the another predetermined number, the process proceeds to step S404. The another predetermined number (i.e., number of frames) may be pre-set. The number of frames may be a function of a minimum gaze time, the minimum gaze time being a minimum time for which a gaze must be detected.

At step S422, a determination is made that the pattern matches (i.e., gaze position is substantially invariant within the tolerance value) and the process ends.

FIG. 5 is a flow chart that shows a method 500 for controlling an electronic device based on real time eye tracking according to one example. At step S502, a camera associated with the electronic device is activated. For example, the front camera of the device is activated.

At step S504, a face is detected in a captured frame. The face detection may be based on the Viola-Jones method, Neural Network-based method, statistical based method, shape based method, example based learning method, wavelet based method, Probabilistic modeling of local appearance methods, spatial relationships based method, or any other suitable method for face detection as would be understood by one of ordinary skill in the art.

In one implementation, when the CPU 600 fails to detect a face, the field of view of the camera may be automatically adjusted and a new frame is captured. Additionally or alternatively, a message may be output to the user on the electronic device screen to adjust the position of the device.

In one implementation, the electronic device 100 may output a signal to an external device when the system fails to detect an eye region or face after a predetermined number of attempts which may indicate that the user is having difficulties adjusting the camera and may need the help of a caregiver.

At step S506, the center of an eye is detected within the face. The system may detect the center of a predefined eye (e.g., right or left eye). In one implementation, the center of the left eye is detected. In one implementation, when the system fails to detect the center of the predefined eye, the system may detect the other eye. The predefined eye may be localized by fitting an elliptical curve to an eye region. The estimates of the fits ellipse routine can be correlated with the shape distribution of the eye if known.

At step S508, the pupil of the eye is detected. For example, the pupil of the predefined eye is detected. The pupil may be detected using model based detection, color based detection, or other suitable detection methods as would be understood by one of ordinary skill in the art. The pupil center and eye center associated with a user may be stored in a database or the memory 602.

In one implementation, step S506 and S508 may be repeated for the other eye detected within the face (e.g., left or right eye).

In the case when using both eyes, a weight may be determined according to the qualities of the left and right eyes detected and may be applied in determining the gaze location. For example, the section of the captured image that includes one of the eyes may have a lower quality (e.g., noise, distortion) than the section including the other eye, due to difference in lighting, or the head position of the user. Thus, the detected center of the eye may have a higher/lower accuracy based on the quality of the section of the captured image. When the quality of the section of the captured image including the left eye is higher than that of the quality of the section of the right eye, the gaze location may be determined by allocating a greater weight to the center of the eye and the center of the pupil of the left eye.

At step S510, the gaze coordinates are determined. In one implementation, the gaze coordinates are determined using equations 5, 6, and 8.

At step S512, a visual indicator is generated on the display of the device at the position associated with the gaze coordinates determined at step S510. The visual indicator is used like a mouse cursor to help a user perform computer functions. The visual indicator is an indication of where the effect of an additional action (e.g., touch) will occur.

At step S514, a gaze pattern is recognized, for example, using the method described in FIG. 4. As described previously herein, the gaze pattern is recognized after a time delay (i.e., position of the pupil is constant in a predetermined number of frames). The time delay provides sufficient time for a user to alter action based on the visual indicator position.

At step S516, a determination is made whether a gaze pattern is recognized. In response to determining that a gaze pattern is recognized the process proceeds to step S518. In response to determining that a gaze pattern is not recognized, the process ends.

At step S518, the average of the pupil position in the predetermined number of frames may be found. At step S520, the gaze position based on the averaged pupil position determined at step S518 is determined.

At step S522, a single touch is injected at the gaze position determined at step S520.

In one implementation, the device can perform various functions based on the detected gaze. For example, various gaze actions may be associated with touch input functions. A gaze to a location outside the display of the device may be mapped to activate sleep, hibernate, or other power saving modes of the device.

Further, gaze at coordinates not associated with a function may trigger an alert to an external device which may indicate that the user is having difficulties using the electronic device 100.

In one implementation, the system may locate the visual indicator at an element in proximity to the actual gaze target, when the actual gaze target is not associated with a function. The element can be a Graphical User Interface (GUI) object, for example, such as a button, text box, menu, or the like. The device can determine which element at which to position the visual indicator based on a weighting system whereby some elements have predetermined weights that are higher than other elements. For example, a button can have a higher weight than a text box. The determination of which element at which to place the visual indicator can also be based on the proximity to the gaze target. For example, the visual indicator is located at the element located nearest to the gaze target.

Further, when the gaze target determined as described previously herein is adjacent to multiple elements (e.g., the gaze target is between two icons on the display screen), the device may generate a zoomed image of a portion of the display located near the user's gaze target. Then, the device may determine a new gaze location.

Although the flow charts show specific orders of executing functional logic blocks, the order of executing the blocks may be changed relative to the order shown, as will be understood by one of ordinary skill in the art. Also, two or more blocks shown in succession may be executed concurrently or with partial concurrence.

The description herein is provided with reference to the system being located and implemented within the electronic device 100. However, it is to be understood that the system may alternatively or additionally be implemented external to the electronic device 100. Further, in some embodiments, the system may be implemented as an application that may be downloaded on the electronic device 100 without the need of any external hardware.

Next, a hardware description of the electronic device 100 according to exemplary embodiments is described with reference to FIG. 6. In FIG. 6, the electronic device 100 includes a CPU 600 which performs the processes described herein. The process data and instructions may be stored in memory 602. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the electronic device 100 communicates, such as a server or computer.

Further, the claimed advancements may be provided as a utility application, background daemon, or component of an operating system, or combination thereof, executing in conjunction with CPU 600 and an operating system such as, Android OS®, Microsoft® Windows®, UNIX®, Oracle® Solaris, LINUX®, Apple macOS™ and other systems known to those skilled in the art.

In order to achieve the electronic device 100, the hardware elements may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the inventive processes described above.

The electronic device 100 in FIG. 6 also includes a network controller 606, such as an Intel Ethernet PRO network interface card from Intel Corporation of America, for interfacing with network 628. As can be appreciated, the network 628 can be a public network, such as the Internet, or a private network such as LAN or WAN network, or any combination thereof and can also include PSTN or ISDN sub-networks. The network 628 can also be wired, such as an Ethernet network, or can be wireless such as a cellular network including EDGE, 3G and 4G wireless cellular systems. The wireless network can also be WiFi® Bluetooth®, or any other wireless form of communication that is known.

The electronic device 100 further includes a display controller 608, such as a NVIDIA® GeForce® GTX or Quadro® graphics adaptor from NVIDIA Corporation of America for interfacing with display 610, such as a Hewlett Packard® HPL2445w LCD monitor. A general purpose I/O interface 612 interfaces with a keyboard and/or mouse 614 as well as an optional touch screen panel 616 on or separate from display 610. General purpose I/O interface also connects to a variety of peripherals 618 including a camera.

A sound controller 620 is also provided in the electronic device 100, such as Sound Blaster® X-Fi Titanium® from Creative, to interface with speakers/microphone 622 thereby providing sounds and/or music.

The general purpose storage controller 624 connects the storage medium disk 604 with communication bus 626, which may be an ISA, EISA, VESA, PCI, or similar, for interconnecting all of the components of the electronic device 100. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

The functions and features described herein may also be executed by various distributed components of a system. For example, one or more processors may execute these system functions, wherein the processors are distributed across multiple components communicating in a network. The distributed components may include one or more client and server machines, which may share processing in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

A system which includes the features in the foregoing description provides numerous advantages to users. In particular, the system provides real-time eye tracking for controlling an electronic device. In addition, the methodologies described herein automatically determine an exact gaze position based on data from either eye or both eyes. Further, the system outputs a signal to an external device when the user is having difficulties using the electronic device. In addition, the system (i.e., modules, functionalities) is not restricted to work on devices with specific operating systems like desktop computers, but is also capable of working on smart devices with different operating systems (e.g., Android OS devices) given the constraints such OS impose on the applications to be run on such devices. Further, the system can run without the use of any external hardware, it can totally depend on the camera integrated in an electronic device. The system provides a non-contact input method to support disabled users who cannot touch the screen of the electronic device. Thus, the system provides a technical solution to a technical problem of and an improvement to the operation of the electronic device. Thus, the system and associated methodology described herein amount to significantly more than an abstract idea based on the improvements and advantages described herein.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The above disclosure also encompasses the embodiments listed below.

(1) A method for controlling an electronic device, the method including receiving, by a processor of the electronic device, a facial image, the facial image including a face of a user having one or more eyes; detecting, in response to detecting an eye within the facial image, a center position of the eye; detecting, in response to detecting an eye within the facial image, a pupil position corresponding to a center of a pupil of the eye; determining, by the processor and based on the center position and the pupil position, an eye gaze position; analyzing the eye gaze position in consecutively captured facial images; and performing a function associated with a touch event at the eye gaze position in response to determining that the gaze position corresponds to a location of the touch event in the consecutively captured facial images.

(2) The method of feature (1), further including displaying a visual indicator on a display of the electronic device at the eye gaze position.

(3) The method of feature (1) or (2), further including providing the visual indicator at an element in proximity of the eye gaze position when the eye gaze position is not associated with a function.

(4) The method of any of features (1) to (3), further including determining the eye gaze position based on a position of the pupil in each of the consecutively captured facial images, determining an average pupil position when there is a match between the pupil position in consecutively captured facial images, and performing the function associated with the touch event at the calculated eye gaze position on a display which is calculated based on the averaged pupil position found in consecutive facial images if a gaze pattern is recognized.

(5) The method of any of features (1) to (4), further including detecting a second eye in the facial image, detecting, in response to detecting a second eye within the facial image, a center position of the second eye and a second pupil position corresponding to the center of the pupil of the second eye, refining the eye gaze position based on the center position of the second eye and the second pupil position, and performing the function associated with the touch event at the refined eye gaze position.

(6) The method of any of features (1) to (5), in which the refining step includes determining a weight corresponding to an image quality of a first section of the facial image including the eye and an image quality of a second section of the facial image including the second eye.

(7) The method of any of features (1) to (6), further including providing soft keys on a display of the electronic device or providing predetermined eye gaze patterns when the eye gaze position is associated with two or more functions.

(8) The method of any of features (1) to (7), in which the eye detected in the facial image corresponds to the left eye.

(9) The method of any of features (1) to (8), further including de e lining a first scaling factor based on a width of the facial image and a width of an eye region detected in the facial image, determining a second scaling factor based on a height of the facial image and a height of the eye region detected in the facial image, scaling the pupil position and the center position of the eye as a function of the first scaling factor and the second scaling factor; determining a displacement between the scaled positions of the pupil position and the center position, and determining the eye gaze position as a function of the displacement and the dimensions of the display of the electronic device.

(10) The method of any of features (1) to (9), further including detecting the face and eye regions using a Haar Cascade classifier.

(11) The method of any of features (1) to (10), further including automatically adjusting a field of view of a camera of the electronic device when the processor fails to detect an eye region in the facial image after a predetermined number of attempts.

(12) The method of any of features (1) to (11), further including outputting a signal to an external device when an eye region is not detected within the facial image after a predetermined number of attempts.

(13) The method of any of features (1) to (12), further including generating a zoomed image of a portion of a display when the eye gaze position is adjacent to multiple elements.

(14) An electronic device including a camera; and a processor configured to detect a center position of an eye within a facial image captured via the camera in response to detecting an eye within the facial image, the facial image including a face of a user having one or more eyes, detect the pupil position of the eye in the facial image in response to detecting an eye within the facial image, determine an eye gaze position based on the center position and the pupil position, analyze the eye gaze position in consecutively captured facial images, and perform a function associated with a touch event at the eye gaze position in response to determining that the gaze position corresponds to a location of the touch event in the consecutively captured facial images.

(15) The electronic device of feature (14), in which the processor is further configured to display a visual indicator on a display of the electronic device at the eye gaze position.

(16) The electronic device of feature (14) or (15), in which the processor is further configured to provide the visual indicator at an element in proximity of the eye gaze position when the eye gaze position is not associated with a function.

(17) The electronic device of any of features (14) to (16), in which the processor is further configured to determine the eye pupil position in each of the consecutively captured facial images, determine an average eye pupil position as a function of the eye pupil positions determined from each of the consecutively captured facial images, and perform the function associated with the touch event at the calculated gaze position determined based on the averaged pupil position and the center of the eye position.

(18) The electronic device of any of features (14) to (17), in which the processor is further configured to detect a second eye in the facial image, detect, in response to detecting a second eye within the facial image, a center position of the second eye and a second pupil position corresponding to the center of the pupil of the second eye, refine the eye gaze position based on the center position of the second eye and the second pupil position, and perform the function associated with the touch event at the refined eye gaze position.

(19) The electronic device of any of features (14) to (18), in which the refining step includes determining a weight corresponding to an image quality of a first section of the facial image including the eye and an image quality of a second section of the facial image including the second eye.

(20) The electronic device of any of features (14) to (19), in which the processor is further configured to provide soft keys on a display of the electronic device or consider predetermined eye gaze patterns, when the eye gaze position is associated with two or more functions.

(21) The electronic device of any of features (14) to (20), in which the eye detected in the facial image corresponds to the left eye.

(22) The electronic device of any of features (14) to (21), in which the processor is further configured to determine a first scaling factor based on a width of the facial image and a width of the eye region detected in the facial image, determine a second scaling factor based on a height of the facial image and a height of the eye region detected in the facial image, scale the pupil position and the center position of the eye as a function of the first scaling factor and the second scaling factor; determine a displacement between the scaled positions of the pupil position and the center position, and determine the eye gaze position as a function of the displacement and the dimensions of the display of the electronic device.

(23) The electronic device of any of features (14) to (22), in which the processor is further configured to detect the face and eye regions using a Haar Cascade classifier.

(24) The electronic device of any of features (14) to (23), in which the processor is further configured to adjust automatically a field of view of a camera of the electronic device when the processor fails to detect an eye region in the facial image after a predetermined number of attempts.

(25) The electronic device of any of features (14) to (24), in which the processor is further configured to output a signal to an external device when an eye region is not detected within the facial image after a predetermined number of attempts.

(26) The electronic device of any of features (14) to (25), in which the processor is further configured to generate a zoomed image of a portion of a display when the eye gaze position s adjacent to multiple elements.

(27) A non-transitory computer-readable medium storing instructions, which when executed by at least one processor cause the at least one processor to perform the method of any of features (1) to (13).

The invention claimed is:

1. A method for controlling an electronic device, the method comprising:

acquiring, by a processor of the electronic device, a facial image, the facial image including a face of a user having one or more eyes;

detecting, in response to detecting an eye within the facial image, a center position of the eye;

detecting, in response to detecting an eye within the facial image, a pupil position corresponding to a center of a pupil of the eye;

determining, by the processor and based on the center position and the pupil position, an eye gaze position as a function of a displacement;

analyzing the eye gaze position in consecutively captured facial images, the analyzing including determining a difference between the pupil position in the consecutively captured facial images; and performing a function at the eye gaze position in response to determining that the eye gaze position corresponds to a location of a touch function in the consecutively captured facial images when the determined eye gaze position is identical in the consecutively captured facial images, wherein the determining the displacement includes applying:

$$\text{Value}_{Scaled} = \text{Max}_{Scaled} \times \log_{10}(\text{Value}_{Unscaled}+1)/\log_{10}(\text{Max}_{Unscaled}+1)$$

where $\text{Value}_{Scaled}$ is the displacement, $\text{Max}_{Scaled}$ is an upper bound of a scaled range of displacement values, $\text{Value}_{Unscaled}$ is a displacement value obtained from an eye region, and $\text{Max}_{Unscaled}$ is the upper bound of an unscaled range of the displacement values.

2. The method of claim 1, further comprising:
displaying a visual indicator on a display of the electronic device at the eye gaze position or at an element in proximity of the eye gaze position when the eye gaze position is not associated with a function of the electronic device.

3. The method of claim 1, further comprising:
determining the pupil position in each of the consecutively captured facial images;
determining an average eye pupil position as a function of the eye pupil positions determined from each of the consecutively captured facial images in response to recognizing that the pupil position in the consecutively captured facial images corresponds to a gaze pattern; and
performing the function at a calculated gaze position determined based on the average eye pupil position and a center position of the eye.

4. The method of claim 1, further comprising:
detecting a second eye in the facial image;
detecting, in response to detecting a second eye within the facial image, a center position of the second eye and a second pupil position corresponding to the center of the pupil of the second eye;
refining the eye gaze position based on the center position of the second eye and the second pupil position; and
performing the function at the refined eye gaze position wherein the refining step includes determining a weight corresponding to an image quality of a first section of the facial image including the eye and an image quality of a second section of the facial image including the second eye.

5. The method of claim 1, further comprising:
providing soft keys on a display of the electronic device and providing predetermined eye gaze patterns, when the eye gaze position is associated with two or more functions.

6. The method of claim 1, further comprising:
determining a first scaling factor based on a width of the facial image and a width of the eye region detected in the facial image;
determining a second scaling factor based on a height of the facial image and a height of the eye region detected in the facial image;
scaling the pupil position and the center position of the eye as a function of the first scaling factor and the second scaling factor;
determining the displacement between the scaled positions of the pupil position and the center position; and
determining the eye gaze position as a function of the displacement and dimensions of a display of the electronic device.

7. The method of claim 6, further comprising:
detecting the face and eye regions using a Haar Cascade classifier.

8. The method of claim 1, further comprising:
automatically adjusting a field of view of a camera of the electronic device when the processor fails to detect an eye region in the facial image after a predetermined number of attempts.

9. The method of claim 1, further comprising:
outputting a signal to an external device when an eye region is not detected within the facial image after a predetermined number of attempts indicating that the user is having difficulties adjusting a camera.

10. The method of claim 1, further comprising:
generating a zoomed image of a portion of a display of the electronic device when the eye gaze position is adjacent to multiple elements of the electronic device.

11. An electronic device comprising:
a camera; and
a processor configured to
detect a center position of an eye within a facial image captured via the camera in response to detecting an eye within the facial image, the facial image including a face of a user having one or more eyes,
detect the pupil position of the eye in the facial image in response to detecting an eye within the facial image,
determine an eye gaze position based on the center position and the pupil position as a function of a displacement,
analyze the eye gaze position in consecutively captured facial images, the analyzing including determining a difference between the pupil position in the consecutively captured facial images, and
perform a function of the electronic device at the eye gaze position in response to determining that the gaze position corresponds to a location of a touch function in the consecutively captured facial images when the determined eye gaze position is identical in the consecutively captured facial images,
wherein determining the displacement includes applying:

$$\text{Value}_{Scaled} = \text{Max}_{Scaled} \times \log_{10}(\text{Value}_{Unscaled}+1)/\log_{10}(\text{Max}_{Unscaled}+1)$$

where $\text{Value}_{Scaled}$ is the displacement, $\text{Max}_{Scaled}$ is an upper bound of a scaled range of displacement values, $\text{Value}_{Unscaled}$ is a displacement value obtained from an eye region, and $\text{Max}_{Unscaled}$ is the upper bound of an unscaled range of the displacement values.

12. The electronic device of claim 11, wherein the processor is further configured to:
display a visual indicator on a display of the electronic device at the eye gaze position.

13. The electronic device of claim 12, wherein the processor is further configured to:
provide the visual indicator at an element in proximity of the eye gaze position when the eye gaze position is not associated with a function of the electronic device.

14. The electronic device of claim 11, wherein the processor is further configured to:
determine the pupil position in each of the consecutively captured facial images;
determine an average eye pupil position as a function of the eye pupil positions determined from each of the consecutively captured facial images in response to recognizing that the pupil position in the consecutively captured facial images corresponds to a gaze pattern; and
perform the function at a calculated gaze position determined based on the average eye pupil position and a center position of the eye.

15. The electronic device of claim 11, wherein the processor is further configured to:
detect a second eye in the facial image;
detect a center position of the second eye and a second pupil position corresponding to the center of the pupil of the second eye in response to detecting a second eye within the facial image;
refine the eye gaze position based on the center position of the second eye and the second pupil position; and
perform the function at the refined eye gaze position.

16. The electronic device of claim 15, wherein the processor is further configured to determine a weight corresponding to an image quality of a first section of the facial image including the eye and an image quality of a second section of the facial image including the second eye.

17. A non-transitory computer readable medium storing computer-readable instructions therein which when executed by a computer cause the computer to perform a method for controlling an electronic device, the method comprising:
receiving a facial image, the facial image including a face of a user having one or more eyes;
detecting, in response to detecting an eye within the facial image, a center position of the eye;
detecting, in response to detecting an eye within the facial image, a pupil position corresponding to a center of a pupil of the eye;
determining, based on the center position and the pupil position, an eye gaze position as a function of a displacement;
analyzing the eye gaze position in consecutively captured facial images, the analyzing including determining a difference between the pupil position in the consecutively captured facial images; and
performing a function at the eye gaze position in response to determining that the gaze position corresponds to a location of a touch function in the consecutively captured facial images when the determined eye gaze position is identical in the consecutively captured facial images, wherein determining the displacement includes applying:

$$\text{Value}_{Scaled} = \text{Max}_{Scaled} \times \log_{10}(\text{Value}_{Unscaled}+1)/\log_{10}(\text{Max}_{Unscaled}+1)$$

where $\text{Value}_{Scaled}$ is the displacement, $\text{Max}_{Scaled}$ is an upper bound of a scaled range of displacement values, $\text{Value}_{Unscaled}$ is a displacement value obtained from an eye region, and $\text{Max}_{Unscaled}$ is the upper bound of an unscaled range of the displacement values.

18. The method of claim 1, further comprising:
   activating a power saving mode of the electronic device when the eye gaze position corresponds to a location outside a display of the electronic device.

19. The method of claim 1, further comprising:
   determining a rooting status of the electronic device indicating whether a user has control over one or more systems of the electronic device;
   outputting an alert to the display of the electronic device when the electronic device is not rooted; and
   initiating a rooting process including downloading a third party rooting tool in response to receiving an acknowledgment from the user via the display.

20. The method of claim 1, wherein the determined eye gaze position is identical in the consecutively captured facial images when the difference is below a tolerance value.

* * * * *